(12) United States Patent
Peterson

(10) Patent No.: US 6,579,221 B1
(45) Date of Patent: Jun. 17, 2003

(54) PROXIMAL CATHETER SHAFT DESIGN AND CATHETERS INCORPORATING THE PROXIMAL SHAFT DESIGN

(75) Inventor: Eric D. Peterson, Fremont, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 61 days.

(21) Appl. No.: 09/872,305

(22) Filed: May 31, 2001

(51) Int. Cl.[7] ............................ A61N 5/00; A61F 11/00
(52) U.S. Cl. ............................................. 600/3; 606/108
(58) Field of Search ........................... 206/366; 606/67, 606/108; 604/91.3, 96.01, 108, 103.01, 264, 524; 600/3

(56) References Cited

U.S. PATENT DOCUMENTS

| | | |
|---|---|---|
| 4,596,563 A | 6/1986 | Pande |
| 4,706,652 A | 11/1987 | Horowitz |
| 4,763,671 A | 8/1988 | Goffinet |
| 4,764,324 A | 8/1988 | Burnham |
| 4,815,449 A | 3/1989 | Horowitz |
| 4,969,863 A | 11/1990 | van't Hooft et al. |
| 5,040,548 A | 8/1991 | Yock |
| 5,046,503 A | 9/1991 | Schneiderman |
| 5,053,044 A * | 10/1991 | Mueller et al. .......... 604/96.01 |
| 5,156,785 A | 10/1992 | Zdrahala |
| 5,190,169 A * | 3/1993 | Sincock .................. 206/366 |
| 5,199,939 A | 4/1993 | Dake et al. |
| 5,209,728 A * | 5/1993 | Kraus et al. .............. 604/913 |
| 5,244,619 A | 9/1993 | Burnham |
| 5,254,107 A | 10/1993 | Soltesz |
| 5,256,144 A * | 10/1993 | Kraus et al. .............. 604/913 |
| 5,267,960 A | 12/1993 | Hayman et al. |
| 5,273,738 A | 12/1993 | Matthews et al. |
| 5,334,169 A | 8/1994 | Brown et al. |
| 5,410,797 A | 5/1995 | Steinke et al. |
| 5,449,343 A | 9/1995 | Samson et al. |
| 5,454,807 A | 10/1995 | Lennox et al. |
| 5,458,613 A | 10/1995 | Charibadeh et al. |

(List continued on next page.)

FOREIGN PATENT DOCUMENTS

| | | | |
|---|---|---|---|
| EP | 0232 074 A2 * | 8/1987 | .......... A61M/20/00 |
| EP | 798008 A2 * | 10/1997 | .......... A61M/16/12 |
| EP | 0 865 803 A2 | 9/1998 | |

OTHER PUBLICATIONS

Abstract 25, "Catheter–Based Radiation in Stented Arteries", Waksman, Ron.

(List continued on next page.)

*Primary Examiner*—Eric F. Winakur
*Assistant Examiner*—Nikita Veniaminov
(74) *Attorney, Agent, or Firm*—Blakely, Sokoloff, Taylor & Zafman LLP (57) ABSTRACT

A novel proximal shaft design used for the manufacture of a catheter. In particular, the proximal shaft design provides excellent stiffness and kink resistance with a reduced outer catheter shaft diameter for improved catheter performance. The proximal shaft design incorporates a shaft with radially extending ridges that have inset regions positioned between adjacent ridges. The catheter may be used in delivering and maintaining a radiation source in a patient's body lumen, such as a coronary artery, for a specified period of time. The proximal shaft design can be applied to other treatments and treatment sources, as well as, other catheter designs.

11 Claims, 7 Drawing Sheets

U.S. PATENT DOCUMENTS

| | | | |
|---|---|---|---|
| 5,480,383 A | | 1/1996 | Bagaoisan et al. |
| 5,484,565 A | | 1/1996 | Larsen et al. |
| 5,516,336 A | | 5/1996 | McInnes |
| 5,520,646 A | | 5/1996 | D'Andrea |
| 5,624,617 A | | 4/1997 | Sorabella |
| 5,653,683 A | | 8/1997 | D'Andrea |
| 5,683,345 A | * | 11/1997 | Waksman et al. ............... 600/3 |
| 5,688,220 A | | 11/1997 | Verin |
| 5,713,828 A | | 2/1998 | Coniglione |
| 5,713,860 A | * | 2/1998 | Kaplan et al. ......... 604/103.01 |
| 5,720,717 A | | 2/1998 | D'Andrea |
| 5,728,042 A | | 3/1998 | Schwager |
| 5,782,740 A | | 7/1998 | Schneiderman |
| 5,816,999 A | | 10/1998 | Bischoff |
| 5,840,008 A | | 11/1998 | Klein et al. |
| 5,855,546 A | | 1/1999 | Hastings et al. |
| 5,860,948 A | | 1/1999 | Buscemi |
| 5,863,284 A | | 1/1999 | Klein |
| 5,882,290 A | | 3/1999 | Kume |
| 5,899,882 A | | 5/1999 | Waksman et al. |
| 5,910,102 A | | 6/1999 | Hastings |
| 5,938,582 A | | 8/1999 | Ciamacco, Jr. et al. |
| 6,004,310 A | | 12/1999 | Bardsley et al. |
| 6,027,475 A | | 2/2000 | Sirhan et al. |
| 6,048,299 A | | 4/2000 | von Hoffmann |
| 6,059,713 A | | 5/2000 | Urick et al. |
| 6,059,748 A | | 5/2000 | Teirstein et al. |
| 6,059,812 A | | 5/2000 | Clerc et al. |
| 6,083,167 A | | 7/2000 | Fox et al. |
| 6,099,454 A | * | 8/2000 | Hastings et al. ............... 600/3 |
| 6,102,890 A | | 8/2000 | Stivland et al. |
| 6,117,064 A | | 9/2000 | Apple et al. |
| 6,129,707 A | | 10/2000 | Cryer |
| 6,142,926 A | | 11/2000 | Schneiderman |
| 6,149,574 A | | 11/2000 | Trauthen et al. |
| 6,149,575 A | | 11/2000 | Leonhardt |
| 6,159,140 A | | 12/2000 | Loeffler et al. |
| 6,165,163 A | | 12/2000 | Chien et al. |
| 6,187,007 B1 | * | 2/2001 | Frigg et al. .................... 606/67 |
| 6,379,365 B1 | * | 4/2002 | Diaz ......................... 606/108 |

OTHER PUBLICATIONS

Abstract 29, "Endovascular Irradiation for Avoidance or Recurrent Stenosis After Stent Implantation in Peripheral Arteries—5 Years Follow–up", Schopohl, B. et al.

Abstract 35, "Catheter Based Beta Radiation System", Weldon, Thomas D.

Abstract 38, "Radioactive Wire in a Self–Centering Catheter System", Popowski, Youri et al.

Abstract 39, "High Dose Rate Afterloader System for Endovascular use–Neocardia", Calfee, Richard V.

Abstract 40, "Issues of Handling Radioactive Devices to Prevent Restenosis", Smith III, Edward F.

Johnson, Lewis W. et al., "Review of Radiation Safety in the Cardiac Catheterization Laboratory", *Catheterization and Cardiovascular Diagnosis*, 25:186–194, 1992.

* cited by examiner

PROXIMAL CATHETER SHAFT DESIGN AND CATHETERS INCORPORATING THE PROXIMAL SHAFT DESIGN

BACKGROUND OF THE INVENTION

This invention relates to catheter shaft design. In particular, the invention relates to a proximal shaft design for intravascular catheters and catheters that incorporate the proximal shaft design. The proximal shaft design is resistant to kinking, maintains sufficient stiffness and can be incorporated into a low profile catheter.

DESCRIPTION OF THE RELATED ART

Catheters are used to place various treatment materials, drugs, and devices within remote target regions of the human body. Catheters designed to traverse the pathways to these target regions typically provide the desired balance between the flexibility required to allow passage of the catheter tip through the tortuous bends of the increasingly narrow blood vessels and the stiffness required to allow the operator to push the catheter tip from the proximal end as the catheter is advanced into the body. The catheter shaft usually has at least two sections, the distal shaft section and the proximal shaft section. The proximal shaft section is usually stiff and provides for the support and push of the catheter during advancement. The distal shaft section on the other hand is usually more flexible and provides for tracking through the vascular pathways. A catheter may have additional sections defined as intermediate shaft sections that provide a gradual transition from the stiffer proximal shaft section to the more flexible distal shaft section.

Some catheters are used to treat coronary vessel narrowing (coronary vessel stenosis). Percutaneous transluminal coronary angioplasty (PTCA), also known as balloon angioplasty, is one of the techniques used for treating stenosis of the coronary arteries. Patients treated by PTCA, however, may suffer from a high incidence of coronary vessel narrowing subsequent to treatment (restenosis), with a significant number of patients requiring treatment for restenosis. In a typical PTCA procedure a guiding catheter is percutaneously introduced into the cardiovascular system of a patient through the brachial or femoral arteries and advanced through the vasculature until the distal end is in the opening of a coronary artery (ostium). In order to reduce the risk of complications, excessive bleeding for example, the physician usually uses a small diameter guiding catheter of 6F or less (F=1 french which is 0.013 inch). More recent devices and procedures for preventing restenosis employ a radiation catheter to deliver a radiation source to minimize or eliminate the cell proliferation implicated in the restenosis process. Radiation catheters are generally larger in diameter than typical dilatation catheters and are one means to deliver and maintain the radiation source in the treatment area.

Many catheters are designed to have the smallest cross-sectional diameter possible to minimize the diameter of guiding catheter needed, thus minimizing the size of the puncture or incision needed to gain access to the body lumen of interest. Additionally, a lower profile catheter may permit access to smaller vessels. Currently, to achieve a minimal profile, provide sufficient stiffness, and maintain sufficient kink resistance, rapid-exchange dilatation catheters utilize stainless steel hypotubes for the proximal catheter shaft. These hypotubes provide the desired properties for a rapid exchange proximal shaft for designs which only require a single inflation lumen with an inner diameter of between 0.010 inch and 0.020 inch. As the inner diameter of the hypotube is increased beyond 0.020 inch, the tube becomes highly susceptible to kinking. Kink resistance of these larger diameter tubes can be improved by increasing the wall thickness of the tubing, but this quickly results in a tube which is too stiff to function as a catheter shaft. Also, the rough, metal inner surface of a typical hypotube, while adequate for use as an inflation lumen, is not appropriate for use in delivering a therapeutic tool, such as a radiation source wire. Some, but not all, of the limitations of a stainless steel hypotube can be overcome through the use of a superelastic nickel-titanium alloy. However, the cost of these super-elastic materials is prohibitive and the inner surface characteristics are not appropriate for delivery of source wires. Thus, these inherent properties of a metal hypotube make it inappropriate for use in designs which require more than a relatively small inflation lumen, that is, inappropriate for designs such as radiation catheters.

An alternate rapid exchange catheter shaft design known in the art is the use of round polymer tubing(s) combined with a metal reinforcing mandrel. While these designs utilizing round extrusions can meet the functional requirements of catheters such as radiation centering catheters, these designs result in large shaft dimensions.

The catheters used in intravascular procedures, particularly to deliver a radioactive source to a target area within the body lumen, may have the following properties for improved performance: a) a source lumen with a lubricious lining b) an inflation/deflation lumen c) sufficient stiffness to allow for support and advancement of the distal end of the catheter d) a resistance to kinking, and e) a minimal cross-sectional area to allow the shaft and guide wire to fit within the guiding catheter with ample space to allow dye injection and other manipulation. A catheter with these general properties should permit access to smaller vessels within the body and improve catheter performance.

One approach to optimizing a catheter is to minimize the thickness of the shaft walls by using a shaft material with increased stiffness. The problem encountered with this approach is that the propensity to kink is increased as the shaft wall thickness is decreased and the material stiffness is increased. The design of a proximal catheter shaft typically balances the need for a small diameter shaft with the requirements for shaft stiffness, while limiting the propensity to kink during catheter advancement.

The current invention addresses the need for a low profile proximal shaft design that provides support and kink resistance during use, as well as other requirements described in the following description.

SUMMARY OF THE INVENTION

The invention is directed to providing a stiff, kink resistant proximal shaft section for a catheter and catheters that incorporate such a proximal shaft. The proximal shaft section design comprises radially extending ridges running longitudinally along the proximal shaft section with inset regions positioned between the radially extending ridges.

DETAILED DESCRIPTION OF THE INVENTION

The present invention describes a novel proximal shaft design for a catheter and catheters incorporating the design. The invention may be incorporated into catheters for use in delivering and/or maintaining a treatment source in a patient's body lumen, such as a coronary artery. In particular, the proximal shaft design can provide a low profile shaft with sufficient stiffness and kink resistance for improved catheter performance. While the invention is described in detail, as applied to radiation treatment of the coronary arteries, those skilled in the art will appreciate that it can also be used in other body lumens and other catheter designs.

Figure 1:
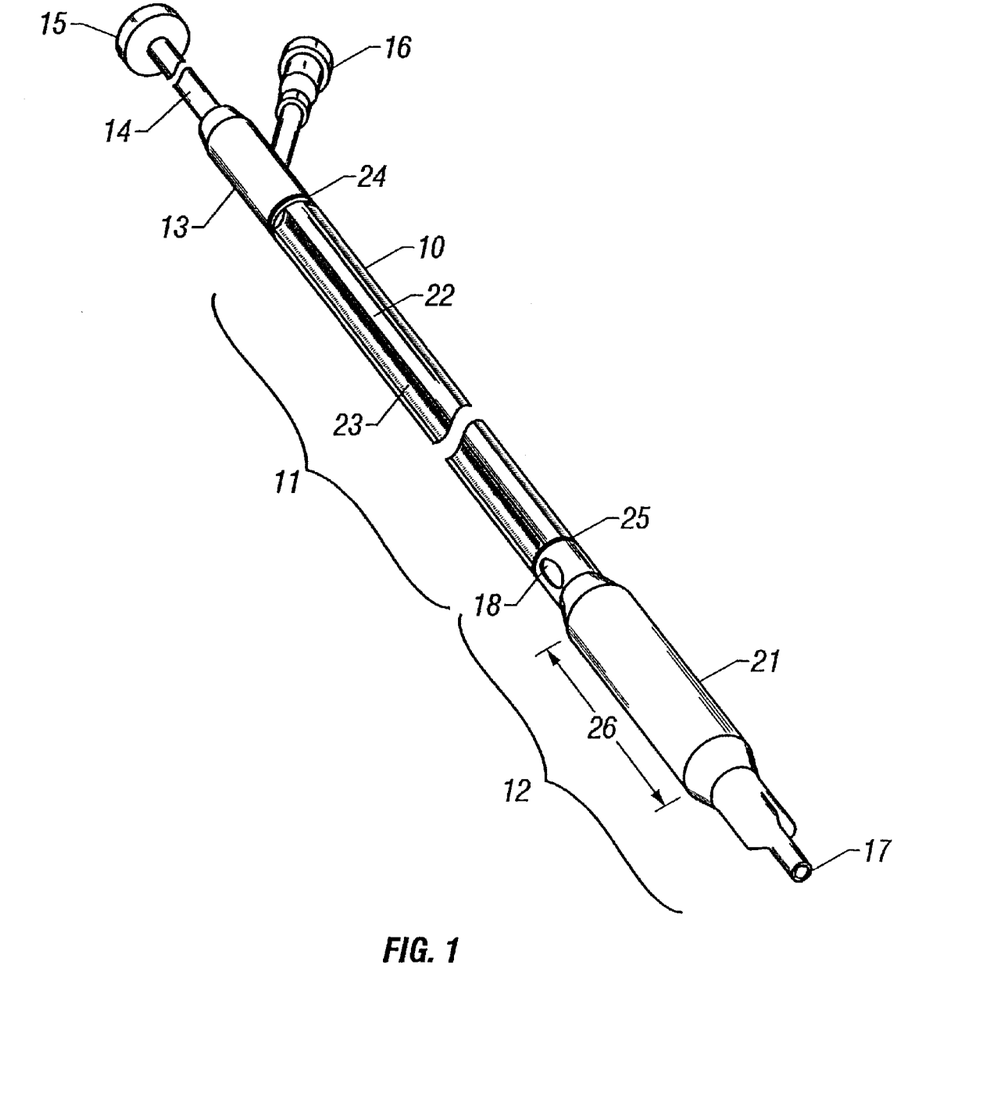
FIG. 1 is a three-dimensional perspective of an embodiment of a rapid exchange (RX) catheter incorporating a proximal shaft design of the invention.

The invention embodies a novel proximal shaft design for a catheter, one embodiment of the invention being a rapid exchange (RX) type catheter. The invention is not limited to incorporation into a RX catheter and can be incorporated into an over the wire type catheter, a tip exchange type catheter, or other catheter designs. An illustration of one embodiment of a proximal shaft design of the present invention incorporated into a basic RX catheter assembly is depicted in FIG. 1. The catheter of FIG. 1 illustrates a catheter shaft 10 having a proximal shaft section 11 joined to a distal shaft section 12 and a proximal adapter or hub 13. The proximal adapter or hub 13 may be joined to a source tube extension 14 and an inflation luer 16. The proximal end of the source tube extension 14 may be joined to a source delivery unit (SDU) connector 15. The distal shaft section 12 may also include a balloon 21 about a distal shaft that may aide in positioning of the catheter for delivery of a treatment source. The distal shaft section may have a distal guide wire port 17 that is fluid communication, via a guide wire tube forming a guide wire lumen, with a proximal guide wire port 18. A guide wire can be slidably disposed within the guide wire lumen to facilitate the rapid advancement and replacement of a catheter assembly.

The proximal shaft section 11 is joined with a proximal adapter 13 and a distal shaft section 12 by conventional joining methods at seals 24 and 25. Such methods include but are not limited to the use of adhesives, laser bonding, and/or shrink wrap seals. Further illustrated in FIG. 1 are radially extending ridges 22 disposed longitudinally along the proximal shaft 11 and inset regions 23 disposed between adjacent radially extending ridges 22. The region of the catheter designated as a treatment region 26 is a region in the distal shaft section that is positioned in the target area (area in need of treatment).

Figure 2:
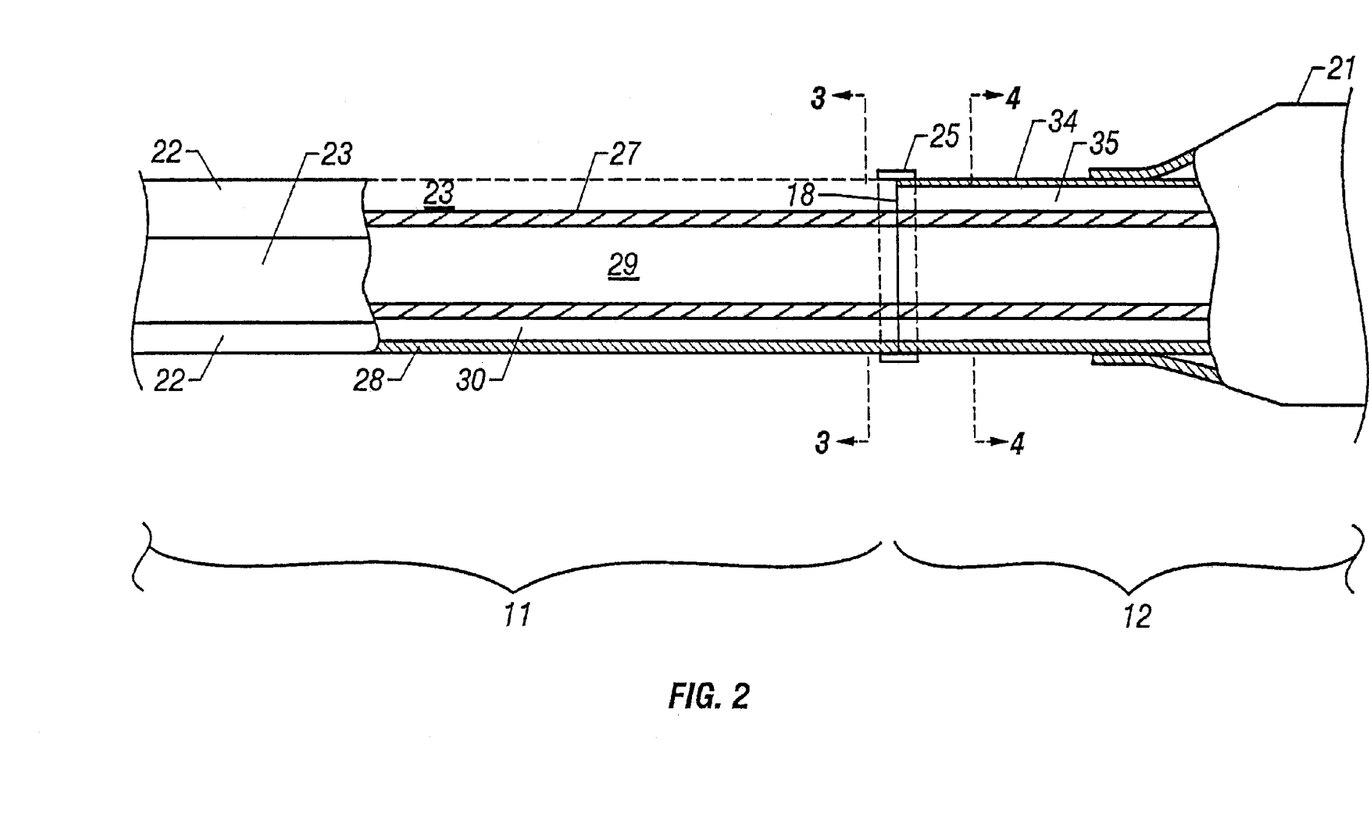
FIG. 2 is a longitudinal cross-sectional view of an embodiment shown in FIG. 1 along a proximal shaft/distal shaft transition.

FIG. 2 illustrates a longitudinal cross-sectional view of a transition region between the proximal shaft 11 and distal shaft 12 sections of the embodiment illustrated in FIG. 1. The proximal shaft section 11 can be abutted against the distal shaft section 12 and sealed with a shrink-wrap seal 25. A treatment source tube 27 and peripheral tube(s) 28 of the proximal shaft and distal shaft are aligned to form a continuous treatment source lumen 29 and peripheral lumen(s) 30. In certain embodiments the peripheral tube 28 having a peripheral lumen 30 may be in fluid communication an inflation luer 16 and a balloon 21. An inset region 23 may be aligned with a guide wire exit port 18 to accommodate the positioning of a guide wire within the inset region 23 along the proximal shaft. A guide wire tube 34 having a guide wire lumen 35 that is in fluid communication with a guide wire exit port 18 and a distal guide wire port 17 may be incorporated into the distal shaft section 12.

Figure 3:
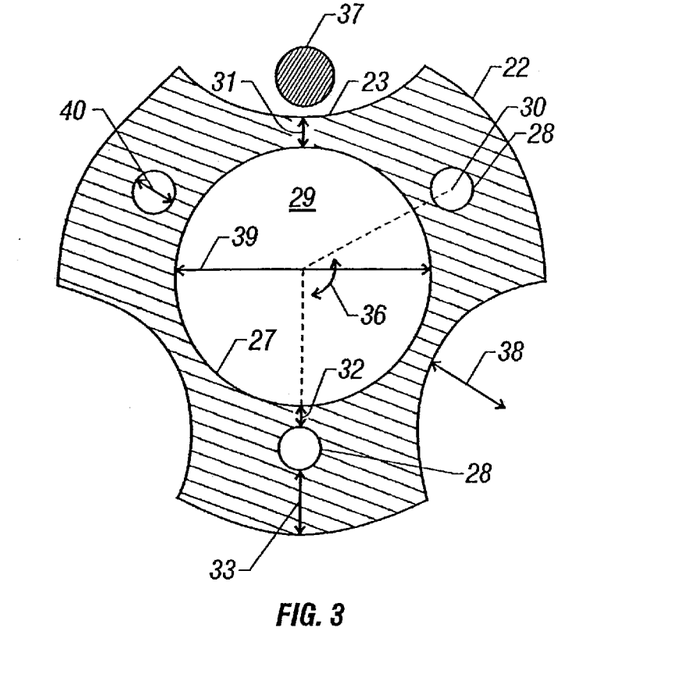
FIG. 3 is a cross-sectional view of FIG. 2 along the line 3—3.

FIG. 3 is a cross-sectional view along line 3—3 of FIG. 2. FIG. 3 shows a proximal shaft section having three radially extending ridges 22. The proximal shaft section also has three inset regions 23 positioned between the radially extending ridges 22. The added strength of the proximal shaft design allows the minimization of the shaft wall 31, the inter-lumen wall 32, the outer wall 33 or a combination of shaft walls allowing for a lower profile catheter. The shaft wall 31 illustrated in FIG. 3 is the shaft material between the treatment source tube 27 and the exterior of the shaft that forms the floor of an inset region 23. Preferably, the shaft wall 31 can be in the approximate range of 0.001 inch to 0.005 inch thick. The outer shaft wall 33 is the shaft material between the peripheral tube 28 and the outer diameter of the shaft. Preferably, the outer shaft wall 33 is typically the thickest wall of a shaft and can be in the preferred approximate range of 0.001 inch to 0.015 inch thick, more preferably in the approximate range of 0.005 inch to 0.010 inch thick. The inter-lumen shaft wall 32 is the shaft material between the treatment source tube 27 and the peripheral tube 28. Preferably, the inter-lumen shaft wall 32 can be in the approximate range of 0.001 inch to 0.005 inch thick.

A four-lumen embodiment as shown in FIG. 3 (a radiation source lumen 29 and three peripheral lumens 30) is exemplary of a structure that provides good column strength with minimal wall thickness, similar to an I-beam structure. In general, the location of the thickest material at the maximum diameter typically increases the bending stiffness of a given cross-section, that is, the shaft maintains longitudinal stiffness but allows lateral bending. Generally, the equiangular positioning of the radially extending ridges 22 in combination with the shaft structure reduces the potential for kinking when the shaft bends. Equiangular positioning of the ridges is preferred but other embodiments are contemplated in which the angle between ridges may vary.

The three radially extending ridges 22 illustrated in the embodiment of FIG. 3 are positioned symmetrically about the proximal shaft 11. The angle 36 between adjacent radially extending ridges 22, in the illustrated embodiment, is approximately 120 degrees. The inset region 23, when aligned with guide wire exit port 18, may also serve as a channel for the guide wire 37 so it can run externally along the proximal shaft section 11 from the guide wire exit port 18 to the proximal end of the proximal shaft 11. The positioning of the guide wire 37 within an inset region 23 aids in profile reduction of the guide wire/catheter combination. In one embodiment, the inset regions 23 will typically have a radius 38 in the preferred approximate range of 0.006 inch to 0.014 inch, more preferably approximately 0.008 inch.

Also depicted in the embodiment illustrated in FIG. 3 is a treatment source tube 27 that is disposed along the shaft and has a treatment source lumen 29, which provides for the advancement of a treatment source through the catheter and into a patients body to a treatment region 26. The treatment source tube 27 can have an inner diameter 39 of, preferably in the approximate range of 0.010 inch to 0.045 inch, more preferably approximately 0.025 inch.

In one embodiment the treatment source tube 27 has a lubricious inner liner that is co-extruded with the shaft. The inner liner is composed of a lubricious material, preferably high density polyethylene (HDPE). Alternative materials for the lubricious inner liner can be polypropylene, polytetrafluoroethylene, ethylene-chlorofluoroethylene, fluorinated ethylene propylene, polychlorotrifluoroethylene, polyvinylfluoride, polyvinylidenefluoride, other lubricious polymers or their mixtures and copolymers.

The treatment region 26 of the shaft is typically a region within the distal shaft section 12 that is positioned within the body lumen at a target area or traumatized region in need of therapy. After treatment the treatment source tube 27 can provide for the withdrawal of a treatment source. The treatment source tube 27 is typically sealed at its distal end, particularly when the treatment source is a radiation source, to prevent entry of any body fluids such as blood, and to provide a sterile barrier between a treatment source and the patient's vascular system. Alternative embodiments may have an open treatment source tube for the direct administration of alternative treatment sources such as drugs, medications and medical devices to a body lumen.

The embodiment diagramed in FIG. 3 further illustrates three peripheral tubes 28 disposed along the catheter shaft 10 having peripheral lumens 30 that are positioned within the shaft external to or outside of the inner diameter of the radiation source tube 27. The term peripheral is used to define the general location of the peripheral tube 28 relative to the source tube 27, thus the peripheral tube 28 is in the periphery or area surrounding the source tube 27. The inner diameter 40 of the peripheral tubes 28 can be, preferably, in the approximate range of 0.004 inch to about 0.020 inch. One or more of the peripheral lumens 30 can serve as inflation/deflation, perfusion, drug delivery, and/or supporting lumens. In an embodiment of the invention illustrated in FIG. 3 there can be one peripheral tube 28 per each radially extending ridge 22, although alternative embodiments may position more than one peripheral tube(s) 28 per radially extending ridge 22 or may have no peripheral tube in some of the radially extending ridges 22. The peripheral lumens 30 may be any shape suitable for inflation/deflation, infusion, perfusion or support. For example, circular, oval, square, elliptical, crescent, rectangle, or other shaped lumens can be used. The peripheral tubes 28 will typically have transverse inner diameters 40 preferably in the approximate range of 0.004 inch to 0.020 inch.

Alternatively, a peripheral tube 28 can be used to provide multiple functions. For example, a peripheral tube 28 may be utilized as a support lumen and an inflation lumen by inserting a hollow mandrel within the peripheral tube 28 and maintaining fluid communication between the balloon 21, peripheral lumen 30 and inflation luer 16 through a lumen in the hollow mandrel. In yet other embodiments the peripheral tube 28 may circumscribe the treatment source tube 27 forming an inflation lumen 30 about the circumference of a treatment source tube 27.

A preferred embodiment of the invention is shown in FIG. 3, although alternative embodiments are contemplated. For example, the number of radially extending ridges can be increased as long as the stiffness and kink resistance of the proximal shaft section are maintained. The number of radially extending ridges may range from 2, 3, 4, 5, 6, or more.

In particular embodiments of the invention the radially extending ridges may be positioned symmetrically about the shaft. Adjacent radially extending ridges can be positioned equiangular to each other. The angle between adjacent radially extending ridges can be approximated by the formula: 360 degrees divided by the number of radially extending ridges. For example, a proximal shaft having four radially extending ridges could have each of the radially extending ridges positioned at about 90 degrees from the adjacent radially extending ridge (360 degrees/4 ridges=90 degrees). Additionally, the number of lumen forming tubes present can vary from 2, 3, 4, 5, 6, or more. Generally a first tube is a treatment source tube with a second tube and so forth being the peripheral tubes.

Figure 4:
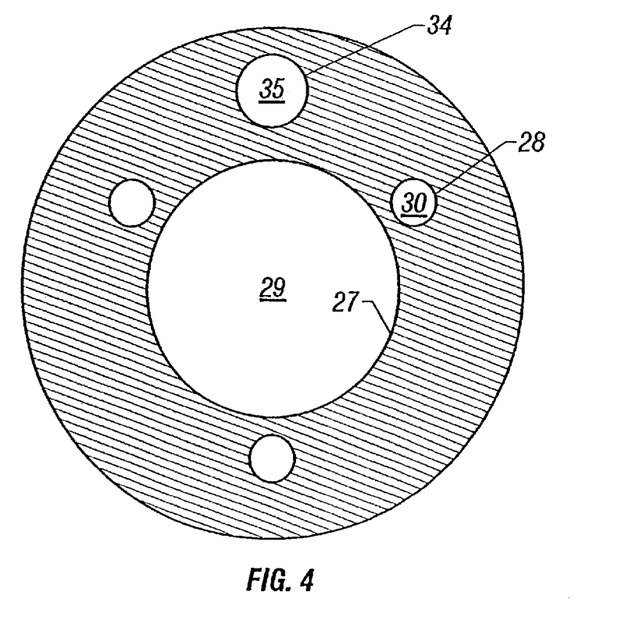
FIG. 4 is a cross-sectional view of FIG. 2 along the line 4—4.

FIG. 4 is a cross-sectional view of FIG. 2 along line 4—4. FIG. 4 illustrates an embodiment of the proximal portion of the distal shaft section 12 distal to the guide wire exit port 18. The distal shaft section 12 provides for the continuation of the treatment source lumen 29 to the treatment area 26, the continuation of the peripheral lumens 30 to the balloon 21 or alternative endpoint depending upon the function of the particular peripheral lumen 30, and a guide wire tube 34 having a guide wire lumen 35 that is in fluid communication with the distal guide wire port 17 and the guide wire exit port 18. The proximal shaft section 11 of the invention may be used in conjunction with a variety of distal shaft 12 configurations. A variety of distal shaft configurations are known and adaptable to the instant invention using conventional methods for joining shaft sections, such as adhesives, shrink wrapping and laser bonding.

Figure 5:
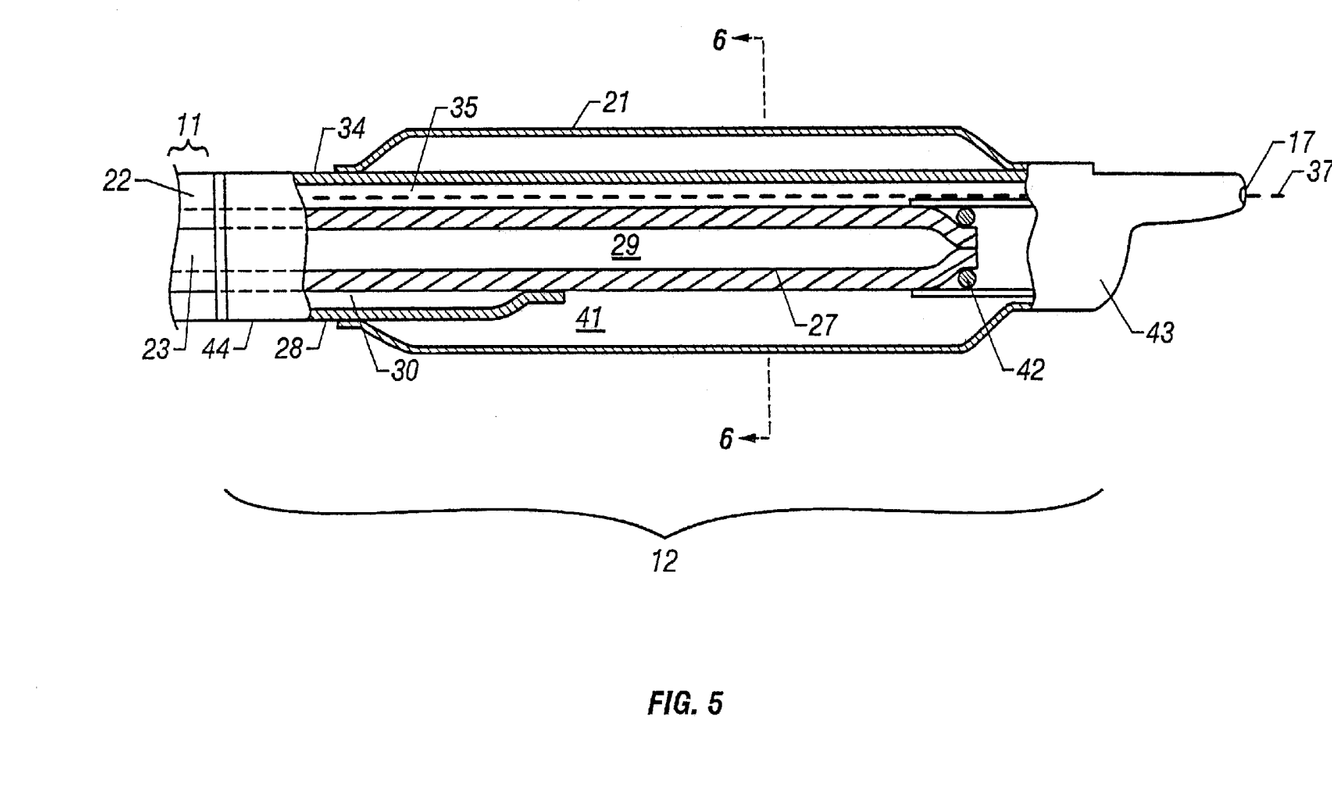
FIG. 5 is a longitudinal cross-sectional view of a distal shaft section embodiment of a RX catheter shown in FIG. 1.

FIG. 5 illustrates a longitudinal cross-sectional view of a distal shaft section of the embodiment illustrated in FIG. 1. The distal end of the treatment source tube 27 is attached to a distal tip assembly 43, a balloon 21, and the proximal portion of a distal shaft section 44. A neck ring 42 is illustrated sealing the distal end of a treatment source tube. Alternative embodiments may use a plug seal, cup seal, other standard tube sealing methods, or a treatment source tube may remain open. A peripheral lumen 30 is typically in fluid communication with an inflation lumen 41 of a balloon 21. A guide wire 37, depicted as a dotted line, is slidably disposed within the guide wire lumen 35 and the distal guide wire port 17. A treatment source tube 27 is shown extending into the distal shaft section 12. Also illustrated in FIG. 5 are radially extending ridges 22 and inset regions 23 of the proximal shaft section 11.

Figure 6:
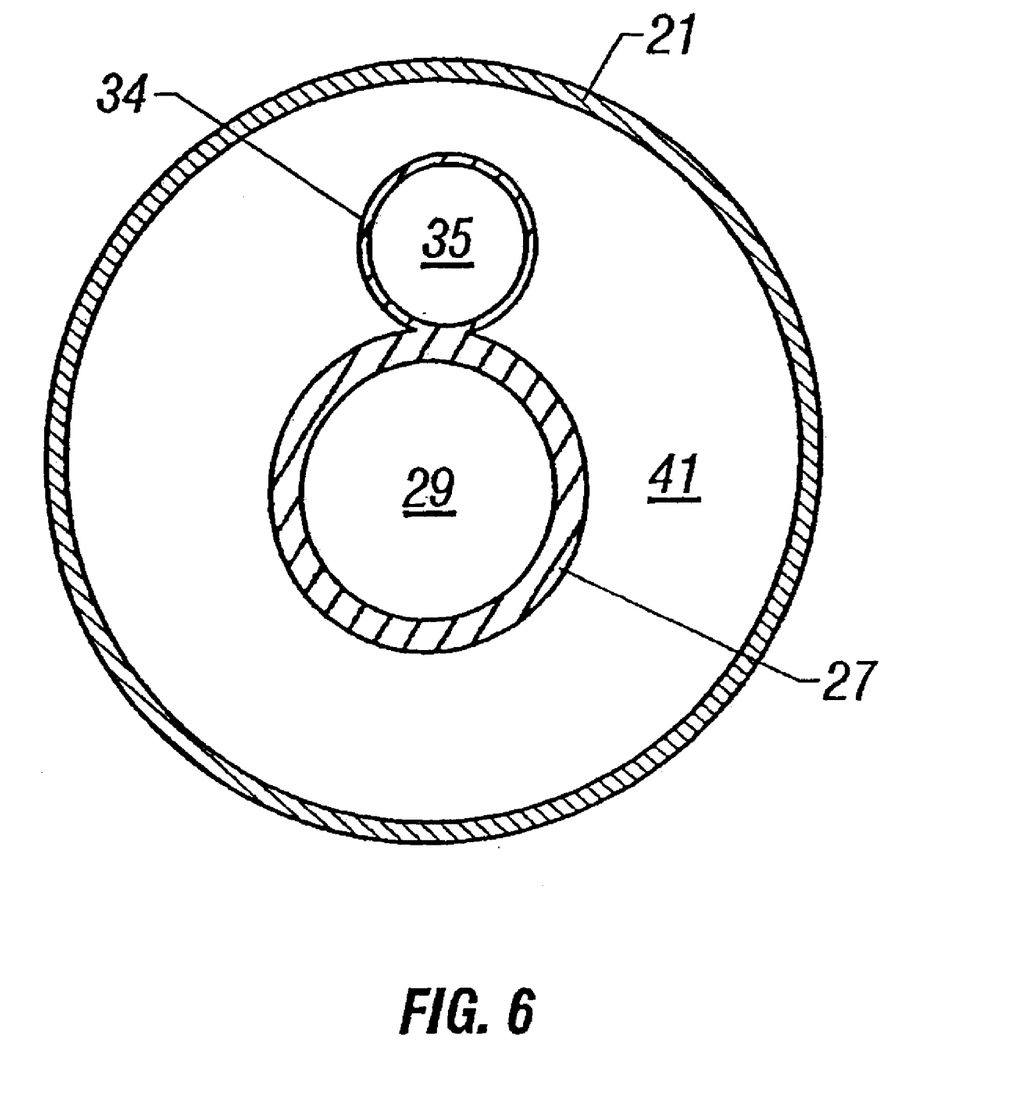
FIG. 6 is a cross-sectional view of a distal shaft of FIG. 5 along line 6—6.

FIG. 6 is a cross-sectional view along the line 6—6 of FIG. 5. Illustrated in FIG. 6 is a distal shaft incorporating a source tube 27, a guide wire tube 34 having a guide wire lumen 35, and a balloon 21 having an inflation lumen 41. A guide wire may be disposed from a distal guide wire port 17 to the guide wire exit port 18 through the guide wire lumen 35. The inflation lumen 41 is in fluid communication with an inflation luer 16 via a peripheral tube 28 having a peripheral lumen 30.

Figure 7:
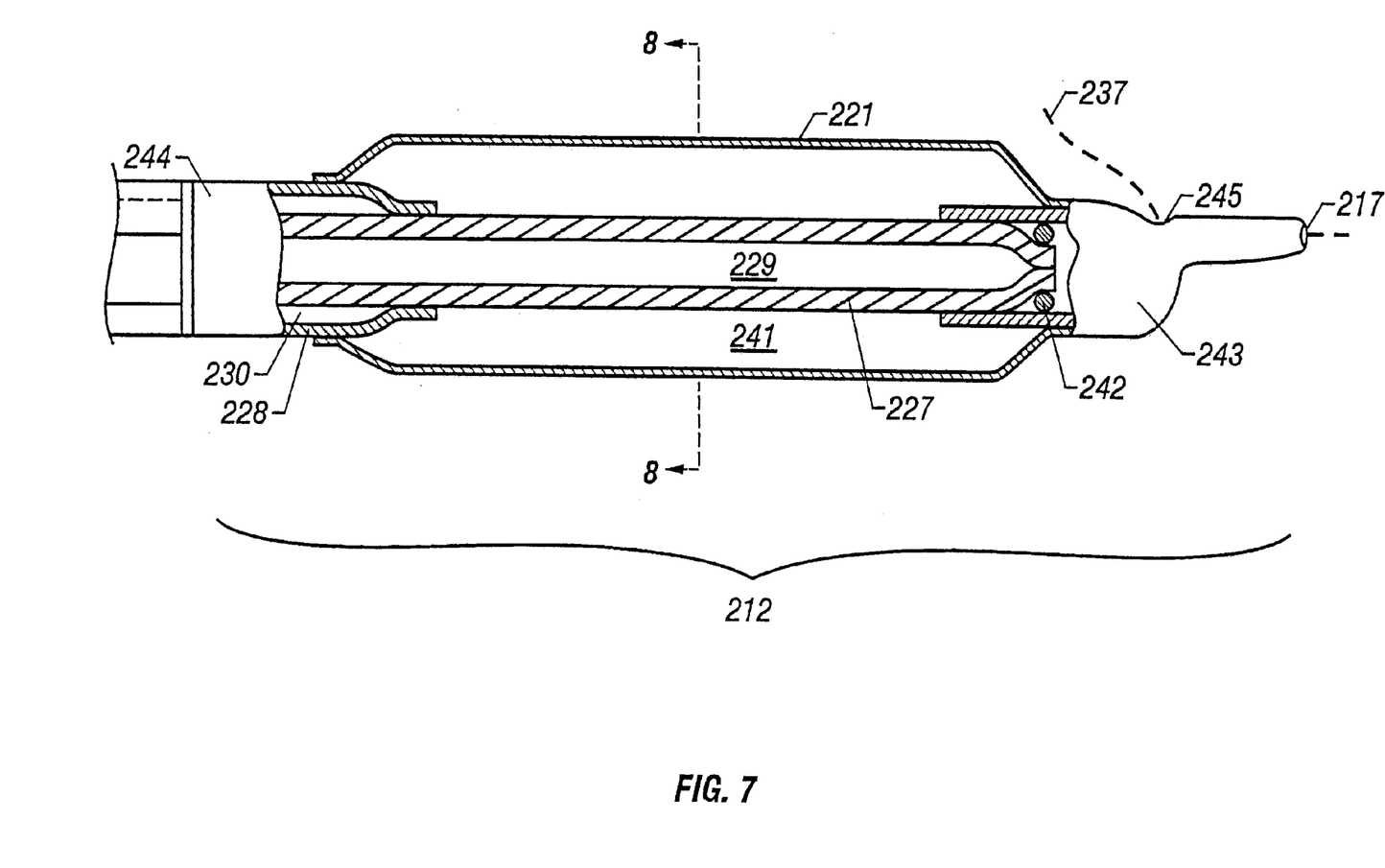
FIG. 7 is a longitudinal cross-sectional view of an alternative embodiment of a distal shaft section.

FIG. 7 illustrates a longitudinal cross-sectional view of an alternative embodiment of a distal shaft section. The distal end of a treatment source tube 227 is attached to a distal tip assembly 243, a balloon 221, and a proximal portion of a distal shaft section 244. A neck ring 242 is illustrated sealing the distal end of the treatment source tube. Alternative embodiments may use a plug seal, cup seal, other standard tube sealing methods, or a source tube may remain open. A peripheral lumen 230 is typically in fluid communication with an inflation lumen 241 of a balloon 221. A guide wire 237, depicted as a dotted line, is slidably disposed in a distal tip assembly 243 between the distal guide wire port 217 and a distal guide wire exit port 245.

Figure 8:
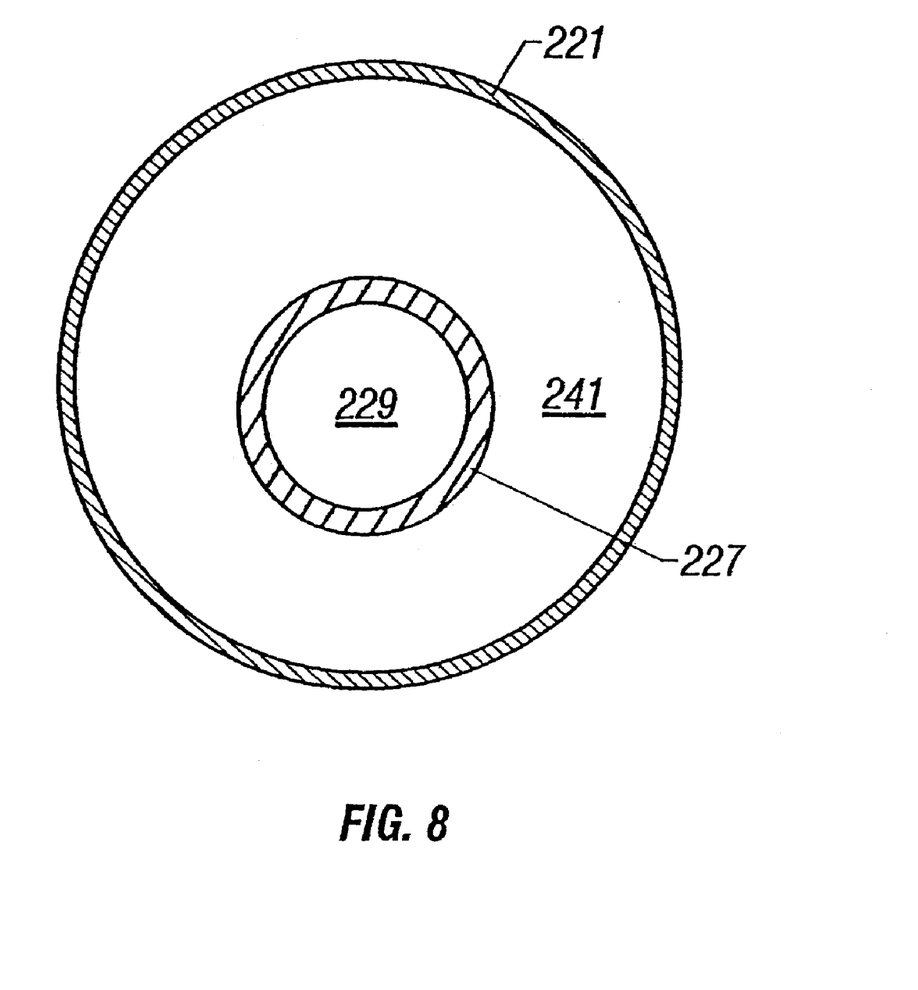
FIG. 8 is a cross-sectional view of a distal shaft of FIG. 7 along line 8—8.

FIG. 8 is a cross-sectional view along the line 8—8 of FIG. 7. Illustrated in FIG. 8 is a distal shaft incorporating a source tube 227 and a balloon 221 having an inflation lumen 241. The inflation lumen 241 is in fluid communication with an inflation luer 16 via a peripheral tube 228 having a peripheral lumen 230.

Catheters incorporating the proximal shaft design may be used to position a treatment section 26 of a catheter in a body lumen. In certain embodiments, a catheter can be used to position a radiation source that is inserted into and advanced along the treatment source lumen where it is maintained in a treatment section of a catheter to provide a radiation dose to a treatment area. Preferably, a radiation source can be a radiation source wire, which is usually hollow at its distal end and can contain a radiation dose in the form of a radiation source, such as pellets, radioactive gas, or radioactive liquid or paste. A radiation source wire may have a radioactive source coated on its distal end. A radiation source wire can provide a sufficient dosage of radiation to the areas of an artery where arterial intervention has been performed (either by PTCA, atherectomy, stenting or other means) to abate the growth of cells in this region.

Generally, the dimensions of the catheter assembly of the present invention are essentially the same dimensions of vascular catheters used in angioplasty procedures. Preferably, the overall length of the catheter may be approximately 100 cm to approximately 175 cm, about 200 cm if the source tube extension is included in the measurement. The diameter of the catheter body may range from preferably about 0.030 inch to 0.090 inch, more preferably about 0.040 inch to about 0.067 inch, yet more preferably 0.040 inch to about 0.050 inch, or most preferably approximately 0.044 inch. The balloon in the unexpanded condition preferably has approximately the same diameter as a catheter body, but may be expanded to a preferred maximum diameter of about 1 to about 5 mm for coronary arteries and substantially larger for peripheral arteries. The diameter of the guide wire lumen should be sufficiently larger than the diameter of guide wire to allow the catheter to be easily advanced and removed over the guide wire. Additionally, the diameter of the radiation source lumen should be sufficiently larger than the diameter of the radiation source wire to allow this device to be easily advanced and removed from within the treatment area.

In a particular embodiment, a method of delivering a radioactive dose to a coronary artery, a guide wire is positioned across the portion of the arterial passageway where a PTCA or atherectomy procedure has been performed. The proximal end of the guide wire is advanced through the interior of the guide wire lumen through distal guide wire port and then out of the guide wire exit port. The catheter is then advanced over the guide wire through a previously positioned guiding catheter to a desired location within the patient's blood vessel, usually where a prior vascular intervention procedure has been performed (the target area). The novel proximal shaft design provides a low profile, kink resistant catheter with sufficient stiffness and strength to advance the catheter over the guide wire to the desired location in the artery. Initially, the balloon is in its unexpanded position to allow the catheter to reach the particular area in the artery.

Once the catheter reaches the desired location, the balloon is expanded with the walls of the balloon coming in contact with the wall of the artery. The radiation source wire can be inserted into the proximal end of the radiation source lumen and advanced until the radiation source, located near the distal end of the radiation source wire, is positioned in the target area. The balloon is held in an expanded condition to allow the radiation dose to affect those cells that may otherwise cause restenosis. Preferably, a sufficient dose of radiation can be delivered from about one minute to about sixty minutes to prevent development of restenosis. In its expanded condition, the balloon or centering balloon presses against, or at least comes in close proximity to, the walls of the artery and in doing so centers the radiation source within the artery. Centering of the radiation dose allows all portions of the artery to receive as close to uniform and equal amounts of radiation as possible. Also, centering helps prevent radiation burns or hot spots from developing on portions of the target area. After the radiation dose has been administered to the body lumen, the radiation source can be removed, the balloon deflated, and the entire catheter assembly withdrawn from the patient's vasculature.

The catheter assembly will typically deliver a dosage of radiation through the body lumen, such as a coronary artery, and is configured to provide the dosage over longer periods of time if necessary. Preferably, 1 to 2 curies may provide a proper dosage level. One of skill in the art has at his or her disposal routine methods of dosage determination and may employ these methods for dosage calculation on a patient-by-patient basis.

In certain embodiments different radiation sources can be used. The preferred radiation sources include but are not limited to iridium$^{192}$ if gamma radiation is used, and phosphorus$^{32}$ if beta particles are used. Further, it is contemplated that the radiation sources may provide beta particles and/or gamma rays to affect the target cells, preferably beta particles. Alternatively, alpha emitting radiation sources also can be used. The use of beta and gamma emitting radiation sources is well known for treating and killing cancerous cells.

In alternative embodiments one or more reinforcing mandrels can be disposed within one or more peripheral tube(s), in order to provide additional support as the catheter is advanced over a guide wire. The mandrel can be a solid or hollow mandrel. In some instances, a reinforcing mandrel may be permanently fixed or enclosed within one or more peripheral lumens, or it may be removable. A mandrel can be fixed within the catheter body by suitable means such as firmly securing the proximal end of the mandrel within an adaptor mounted on the proximal end of the catheter body. Also, the mandrel may have several sections that have sequentially smaller diameters (sequentially smaller diameters in the distal direction). Sequentially smaller diameters can be provided with tapers between the various-sized sections. This allows varying degrees of strength and flexibility up to the catheter shaft as is necessary. One option is that the distal 10 to 40 cm of the mandrel will have reduced dimensions obtained, for example, by a continuous or stepwise grinding profile. Generally, more gradual changes in dimension are utilized to provide stiffness for advancement of the catheter tip and provide trackability. Further details of the construction of reinforcing mandrels can be found in the art.

In another alternative embodiment of the invention the catheter assembly may incorporate a tip rapid exchange (RX) configuration. The catheter assembly has a guide wire lumen in which the second guide wire exit port is located distal to the balloon 19. In this particular embodiment, the length of the guide wire lumen is preferably in the approximate range of 0.3 cm to 2.5 cm.

Alternatively, spiral or ribbed balloons, or other similar centering means, could be employed to allow perfusion over or through the centering means. For example, an expandable metal cage could be used as a centering device. Such a cage would allow blood flow through the lattice of the cage. In yet another alternative embodiment the proximal shaft section of the invention is used in conjunction with a distal shaft section that incorporates a multi-lumen balloon. One or more peripheral lumens can be in fluid communication with the inflation lumens of the balloon. A further alternative is having a peripheral lumen individually and separately in communication with a distinct inflation lumen of the balloon. This configuration would allow each of the balloon lumens to be inflated individually and lend greater control to the centering of the radiation source.

A catheter incorporating the invention as described herein is generally employed after an atherectomy, percutaneous transluminal coronary angioplasty procedure, or stent implantation to allow a radiation dose to be administered to an area where restenosis might otherwise develop in the coronary artery. It should be recognized by those skilled in the art that the catheter of the present invention can be used within a patient's vascular system after vascular procedures other than a PTCA, a stent implantation or an atherectomy have been performed.

The catheters incorporating the present invention may be formed of conventional materials of construction that are described in detail in the art. The proximal shaft section can be manufactured by multi-lumen extrusion using a high-strength polymer such as poly ether ether ketone (PEEK) or preferably nylon. A preferred embodiment of the invention utilizes co-extrusion with the proximal shaft to provide a lubricious inner liner to the source tube. The preferred material for the inner liner is high density polyethylene (HDPE). The various components of the catheter may be joined by suitable adhesives such as the acrylonitrile based adhesive sold as Loctite 405. Heat shrinking, laser bonding or heat bonding may also be employed where appropriate. A suitable adhesive such as Loctite 405 can effect plastic-to-plastic or plastic to metal joints.

Reinforcing mandrel(s) can be made from a stainless steel, NiTi alloys, or other suitable materials such as high strength plastic. The tapers and small diameter portions of the mandrel can be formed in the same manner as that used in forming small diameter sections on guide wires, e.g., centerless grinding. Additionally, the radiation source wire can be made from similar materials such as stainless steel, titanium, nickel titanium and platinum nickel alloys or any suitable polymers and composites. Other modifications can be made to the present invention without departing from the spirit and scope thereof. The dimensions, doses, times and materials of constructions are provided as examples and substitutes are readily contemplated which do not depart from the invention.

What is claimed:

1. A catheter comprising:
a longitudinal shaft having a proximal shaft section, said proximal shaft section having radially extending ridges running longitudinally along said proximal shaft section, said proximal shaft section defining a treatment source tube having a treatment source lumen therethrough running longitudinally along said proximal shaft section, wherein said treatment source tube has a lubricious inner liner formed by co-extrusion with said proximal shaft section.

2. The catheter of claim 1, wherein said lubricious inner liner is fabricated from high density polyethylene.

3. The catheter of claim 1, wherein said proximal shaft section defines at least one peripheral tube having a peripheral lumen therethrough running longitudinally along said proximal shaft.

4. The catheter of claim 3, wherein a mandrel is disposed in a peripheral tube.

5. A catheter comprising:
a longitudinal shaft having a proximal shaft section, said proximal shaft section having a radiation source tube running longitudinally with a radiation source lumen therethrough, said proximal shaft section having at least one peripheral tube running longitudinally having a peripheral lumen therethrough, wherein said proximal shaft section has three radially extending ridges that are positioned at an approximate angle of 120 degrees with respect to adjacent radially extending ridges.

6. The catheter of claim 5, wherein said radiation source tube has a lubricious inner liner formed by co-extrusion with said proximal shaft section.

7. A radiation catheter comprising:
a longitudinal shaft having a proximal shaft section and a distal shaft section;
said proximal shaft section having three radially extending ridges running longitudinally along said proximal shaft section;
said distal shaft section having a distal guide wire port;
a guide wire exit port proximate to said distal guide wire port;
a guide wire lumen between said distal guide wire port and said guide wire exit port;
a radiation source tube having a distal seal, said radiation source tube having a radiation source lumen therethrough; and
a balloon mounted on said distal shaft section, said balloon is in fluid communication with a proximal inflation luer through at least one peripheral lumen, wherein said radially extending ridges are positioned at an approximate angle of 120 degrees with respect to adjacent radially extending ridges.

8. The radiation catheter of claim 7, wherein said Proximal shaft section has four lumens running longitudinally along said proximal shaft section;
a first radiation source lumen located within said proximal shaft section; and
a second, third, and fourth peripheral lumens located within said proximal shaft section and disposed external to said radiation source lumen within said radially extending ridges.

9. The catheter of claim 8, wherein said radiation source tube has a lubricious inner liner formed by co-extrusion with said proximal shaft section.

10. A method comprising:
providing a catheter having a longitudinal shaft, a proximal portion of the longitudinal shaft having radially extending ridges running longitudinally along the longitudinal shaft;
inserting the longitudinal shaft in a body lumen until a treatment section is positioned within a target area;
inserting a radioactive source into the treatment section, to emit radiation at the target area; and
leaving the radioactive source in place for a predetermined period of time to enable radiation from the radioactive source to pass into the target area, wherein the proximal portion has three radially extending ridges.

11. The method of claim 10, wherein said radially extending ridges are positioned at an approximate angle of 120 degrees with respect to adjacent radially extending ridges.

* * * * *